United States Patent
Iizuka et al.

(10) Patent No.: US 10,405,798 B2
(45) Date of Patent: Sep. 10, 2019

(54) BIO-INFORMATION DETECTING APPARATUS

(71) Applicant: TOYOTA JIDOSHA KABUSHIKI KAISHA, Toyota-shi (JP)

(72) Inventors: Hisashi Iizuka, Susono (JP); Hirokazu Kikuchi, Hadano (JP)

(73) Assignee: TOYOTA JIDOSHA KABUSHIKI KAISHA, Toyota-shi (JP)

( * ) Notice: Subject to any disclaimer, the term of this patent is extended or adjusted under 35 U.S.C. 154(b) by 346 days.

(21) Appl. No.: 15/254,691

(22) Filed: Sep. 1, 2016

(65) Prior Publication Data
US 2017/0055904 A1    Mar. 2, 2017

(30) Foreign Application Priority Data

Sep. 2, 2015    (JP) .................................. 2015-172614

(51) Int. Cl.
*A61B 5/00*    (2006.01)
*A61B 5/0408*    (2006.01)
(Continued)

(52) U.S. Cl.
CPC ........ *A61B 5/6822* (2013.01); *A61B 5/02416* (2013.01); *A61B 5/02438* (2013.01);
(Continued)

(58) Field of Classification Search
CPC . A61B 5/0205; A61B 5/1455; A61B 5/14551; A61B 5/14552; A61B 5/14553;
(Continued)

(56) References Cited

U.S. PATENT DOCUMENTS

| 4,859,057 A * | 8/1989 | Taylor ................ A61B 5/14551 600/473 |
| 2002/0028991 A1* | 3/2002 | Thompson ........... A61B 5/0006 600/372 |

(Continued)

FOREIGN PATENT DOCUMENTS

FR    2 748 928 A1    11/1997
JP    2003-325466 A    11/2003
(Continued)

OTHER PUBLICATIONS

Extended European Search Report dated Jan. 17, 2017 in patent application No. 16186664.5.

*Primary Examiner* — Eric F Winakur
*Assistant Examiner* — Chu Chuan Liu
(74) *Attorney, Agent, or Firm* — Oblon, McClelland, Maier & Neustadt, L.L.P.

(57) ABSTRACT

A bio-information detecting apparatus includes: a band member curved in a C-shape, and attached around a neck part of an examinee from a back side of the neck part; and a pair of electrodes for cardiac potential measurement disposed at positions on the band member that come into contact with right and left skin surfaces of the neck part, and in the pair of electrodes, a position of the electrode on the right is located relatively more frontward than a position of the electrode on the left. The bio-information detecting apparatus further includes a substrate to optically measure a blood oxygen saturation for pulse measurement at a position on the band member that comes into contact with the neck part of the examinee, and a pressing force of the substrate against the skin surface of the neck part is 0.96 to 1.21 [$N/cm^2$].

7 Claims, 5 Drawing Sheets

(51) Int. Cl.
    *A61B 5/1455*   (2006.01)
    *A61B 5/024*    (2006.01)
    *A61B 5/0402*   (2006.01)

(52) U.S. Cl.
    CPC ........ *A61B 5/0402* (2013.01); *A61B 5/04085* (2013.01); *A61B 5/14551* (2013.01); *A61B 5/14552* (2013.01); *A61B 5/6831* (2013.01); *A61B 2562/0209* (2013.01); *A61B 2562/0238* (2013.01); *A61B 2562/063* (2013.01)

(58) Field of Classification Search
    CPC . A61B 5/02438; A61B 5/6822; A61B 5/3831; A61B 5/04085; A61B 5/04087; A61B 5/02416
    See application file for complete search history.

(56) References Cited

U.S. PATENT DOCUMENTS

| | | | |
|---|---|---|---|
| 2005/0038356 A1* | 2/2005 | Fortin | A61B 5/04087 600/582 |
| 2010/0137726 A1 | 6/2010 | Matsumura | |
| 2012/0108939 A1 | 5/2012 | Matsumura | |
| 2014/0236031 A1 | 8/2014 | Banet et al. | |
| 2015/0099982 A1 | 4/2015 | Fujisaki | |
| 2015/0148618 A1 | 5/2015 | Sitko et al. | |

FOREIGN PATENT DOCUMENTS

| | | |
|---|---|---|
| JP | 2007-202939 A | 8/2007 |
| JP | 2008-161657 A | 7/2008 |
| JP | 2015-073557 A | 4/2015 |

* cited by examiner

BIO-INFORMATION DETECTING APPARATUS

INCORPORATION BY REFERENCE

The disclosure of Japanese Patent Application No. 2015-172614 filed on Sep. 2, 2015 including the specification, drawings and abstract is incorporated herein by reference in its entirety.

BACKGROUND OF THE DISCLOSURE

1. Field of the Disclosure

The present disclosure relates to an apparatus to measure bio-information. Particularly, the present disclosure relates to an apparatus to measure bio-information regarding human heartbeats, such as cardiac potential and pulse waves, and more specifically, to a neck-band type bio-information detecting apparatus attached around a human neck part.

2. Description of Related Art

There have been developed techniques of promoting reduction in dimension of sensors capable of measuring bio-information regarding human heartbeats, such as cardiac potential and pulse waves, and transmitting measurement values of these sensors via radio communication. Therefore, there have been proposed various portable bio-information detecting apparatuses attached to heads, necks, or the like of examinees so as to allow the examinees to relatively freely take exercise. For example, in Japanese Patent Application Publication No. 2003-325466, proposed is a bio-information detecting apparatus configured to include electrodes coming into contact with a neck part of an examinee so as to detect cardiac potential of the examinee, at both ends of a C-shaped neck band attached to the examinee from the back side of his or her neck part, and transmit the potential difference of the electrodes to the outside via radio communication. Japanese Patent Application Publication No. 2007-202939 discloses a configuration that provides both ends of a C-shaped neck band as described above with not only measurement means of cardiac potential, but also sensor means to optically measure blood oxygen saturation in the carotid artery of an examinee so as to detect his or her pulse waves. Furthermore, Japanese Patent Application Publication No. 2015-73557 discloses a configuration that provides a C-shaped neck band attached to an examinee from the back side of his or her neck part with sensor means to optically measure blood oxygen saturation, in particular, a bio-information detecting apparatus configured to include cardiac potential measurement means and pulse wave detecting means to optically measure blood oxygen saturation on a C-shaped neck band of the apparatus attached from the back side of a neck part has an advantage in that the apparatus has a smaller dimension, and does not cause much influence on any exercise taken by an examinee.

One of current challenges in bio-information detecting apparatuses including measurement means to measure cardiac potential and pulse waves on neck bands attached around neck parts is to measure cardiac potential and blood oxygen saturation with as high measurement sensitivity as possible. For example, if cardiac potential is measured at a neck part, its measurement part is located apart from a heart; thus measurement sensitivity becomes considerably deteriorated compared with the case of measuring cardiac potential at a chest part near the heart. Actually, cardiac potential measuring means of a type that has electrodes at both ends of a neck band detects considerably smaller amplitudes of measurement values of cardiac potential. When a neck band is attached around a neck part, elasticity of the neck band is utilized so as to prevent the neck band from dropping off the neck. However, depending on the degree of pressure onto a vessel with too strong elasticity, it is confirmed that some influence might be caused to amplitudes of measurement values of pulse waves (blood oxygen saturation). Hence, in above described neck-band type bio-information detecting apparatuses attached around neck parts, it is preferable to improve configurations thereof in order to improve measurement sensitivity of cardiac potential and pulse waves.

SUMMARY OF THE DISCLOSURE

Accordingly, one of challenges of the present disclosure is to provide a novel configuration to improve sensitivity of measurement values of cardiac potential and blood oxygen saturation in a bio-information detecting apparatus having measurement means of cardiac potential and pulse waves in a neck band attached around a neck part.

According to one aspect of the present disclosure, a bio-information detecting apparatus is provided, and the bio-information detecting apparatus includes: a band member curved in a C-shape, the band member attached in a manner as to extend along a neck part of an examinee from a back side of the neck part toward both lateral sides of the neck part; and a pair of electrodes for cardiac potential measurement of the examinee, the pair of electrodes disposed at positions of the band member that come into contact with right and left skin surfaces of the neck part of the examinee, wherein, of the pair of electrodes, a position of the electrode located on the right of the examinee is located relatively more frontward than a position of the electrode located on the left of the examinee. In the above configuration, as is easily understood with reference to drawings of embodiments described later, the "band member curved in a C-shape" denotes a member having a neck band structure attached from the back side of the neck part of the examinee, and typically is formed by a flexible or elastic material, such as a plastic material that has been commonly used in this field. The "pair of electrodes for cardiac potential measurement" may be electrode pieces commonly used in this field, and each of the electrodes has a dimension of approximately several mm to 2 cm, which is large enough for measuring the cardiac potential.

As aforementioned, in the bio-information detecting apparatus of the present disclosure, the "pair of electrodes for cardiac potential measurement" is arranged on the "band member" in a manner as to be in contact with the right and left skin surfaces of the neck part of the examinee, and the positions of the electrodes are arranged in such a manner that the electrode located on the right of the examinee is disposed relatively more frontward than the position of the electrode located on the left of the examinee. As described later in the column of the embodiment, if the pair of electrodes are arranged on the band member, various configurations of electrode arrangement along the band member may be considered; and according to experiments conducted by the inventors of the present invention, it has been found that if the electrode on the right is disposed more frontward than die electrode on the left, the amplitude of the measured cardiac potential becomes considerably greater than that in the other cases, thereby measuring the cardiac potential in a preferable manner. In the apparatus of the present disclosure, as aforementioned, the electrode located on the right of the examinee is disposed relatively more frontward than the position of the electrode located on the left of the examinee, thereby increasing the measurement sensitivity of the cardiac potential. It has also been found that if the electrode located on the right is disposed in a more frontward region on the band member than the right lateral side of the neck part of the examinee, and the electrode located on the left is disposed at a more backward position on the band member than the left lateral side of the neck part of the examinee, the amplitude of the measured cardiac potential becomes the maximum. Hence, more preferably, in the apparatus of the disclosure, as aforementioned, the electrode on the right may be disposed in a more frontward region on the band member than the right lateral side of the neck part of the examinee, and the electrode on the left may be disposed at a more backward position on the band member than the left lateral side of the neck part of the examinee.

In the above electrodes, it may be configured that each contact surface of the pair of electrodes that comes into contact with the skin surface of the neck part of the examinee is in a flat state or in a curved state in a direction in which a center portion of the contact surface protrudes more than a peripheral edge of the contact surface toward the skin surface of the neck part of the examinee, the protrusion being within a range of not more than 1 mm. With respect to the contact surface of each electrode, in order to bring each electrode to stably contact with the neck part of the examinee, for example, it is considered to be preferable that the contact surface of each electrode with the skin surface of the neck part of the examinee is formed to be curved such that the center portion of the contact surface protrudes more than the peripheral edge thereof toward the skin surface of the neck part of the examinee so as to securely contact with the skin surface of the neck part. According to the experiments, it has been found that the amplitude of the measured cardiac potential is detected with the most excellent sensitivity, and if the center portion of the contact surface protrudes more than the peripheral edge thereof by more than 1 mm toward the skin surface of the neck part of the examinee, the amplitude of the measured cardiac potential becomes significantly decreased compared with the case of the contact surface having a flat shape. In the present disclosure, preferably, it may be configured that the contact surface of each electrode that comes into contact with the skin surface of the neck part of the examinee is in a flat state or in a curved state in a direction in which a center portion of the contact surface protrudes more than a peripheral edge thereof toward the skin surface of the neck part of the examinee, the protrusion being within a range of not more than 1 mm.

Furthermore, with respect to the aforementioned electrodes, according to the experiments, it has been found that if the contact area of each electrode with the skin surface of the neck part of the examinee is less than 25 mm$^2$, the measurement sensitivity to the amplitude of the cardiac potential becomes significantly decreased. Hence, in the above described present disclosure, preferably, a contact area of each of the pair of electrodes that comes into contact with the skin surface of the neck part of the examinee may be more than 25 mm$^2$.

According to another aspect of the present disclosure, a bio-information detecting apparatus is provided and includes: a band member curved in a C-shape, the band member attached in a manner as to extend along a neck part from a back side of the neck part toward both lateral sides of the neck part to a region more frontward than the lateral side of the neck part; and a substrate disposed at a position on the band member that comes into contact with the neck part of the examinee, the substrate having a light emitting part and a light receiving part that are used for optically measuring a blood oxygen saturation for pulse measurement of the examinee, wherein in a state in which the substrate is in contact with a skin surface of the neck part of the examinee, a pressing force of the substrate against the skin surface of the neck part is 0.96 to 1.21 [N/cm$^2$]. The "substrate having a light emitting part and a light receiving part used for optically measuring blood oxygen saturation for pulse measurement" may be any sensor unit optically measuring the blood oxygen saturation in this field, as described in JP 2007-202939 A, for example. With respect to such a substrate for the pulse measurement, there might be considered various factors to cause influence on the magnitude of the amplitude of the blood oxygen saturation that is a measurement value obtained when the substrate comes into contact with the skin surface of the examinee. According to the studies by the inventors of the present disclosure, it has been found that the magnitude of the amplitude of the blood oxygen saturation depends on the pressing force of the sensor unit. In particular, it has been found that the pressing force falls within a range of 0.96 to 1.21 [N/cm$^2$], the amplitude of the blood oxygen saturation becomes increased, and the change in blood oxygen saturation, that is, the pulse can be detected with a preferable sensitivity. Hence, as aforementioned, in the present disclosure, in a state in which the substrate is in contact with a skin surface of the neck part of the examinee, a pressing force of the substrate against the skin surface of the neck part is 0.96 to 1.21[N/cm$^2$]. Such a pressure adjustment can be achieved by adjusting the elastic force of the band member when the band member is attached around the neck part of the examinee.

The configuration of setting the pressing force of the substrate for the pulse measurement to be within a range of 0.96 to 1.21 [N/cm$^2$] may be applicable to the bio-information detecting apparatus including the configuration regarding the aforementioned electrodes for the cardiac potential measurement. According to this configuration, it is possible to hold the apparatus having the band-like structure curved in a C-shape against the neck part in a manner as not to be out of position by the electrodes and the substrate, thereby measuring both the cardiac potential and the pulse with an excellent sensitivity, which results in advantage.

As aforementioned, in the configuration of the above described present disclosure, it is possible to measure cardiac potential and pulse pertinent to human heartbeats with a more excellent sensitivity through the neck-band type apparatus attached around a human neck part, compared with the conventional configuration. The neck-band type apparatus attached around a human neck part is portable and allows measurement at portions of an examinee regardless of accessories and clothes, which results in advantage. According to the present disclosure, it is expected to improve measurement accuracy of cardiac potential and pulse in a neck-band type bio-information detecting apparatus as above configured, and it is also expected to facilitate measurement of cardiac potential and pulse more than the conventional one, and promote increase in opportunity to use the apparatus.

The other objects and advantages of the present disclosure will be revealed by the following description of preferable embodiments of the present disclosure.

BRIEF DESCRIPTION OF THE DRAWINGS

Features, advantages, and technical and industrial significance of exemplary embodiments of the disclosure will be described below with reference to the accompanying drawings, in which like numerals denote like elements, and wherein.

DETAILED DESCRIPTION OF EMBODIMENTS

Several preferable embodiments of the present disclosure will be described with reference to accompanying drawings, hereinafter. In the following drawings, the same reference numerals indicate the same parts.

Basic Configuration of Bio-Information Detecting Apparatus

Figure 1A:
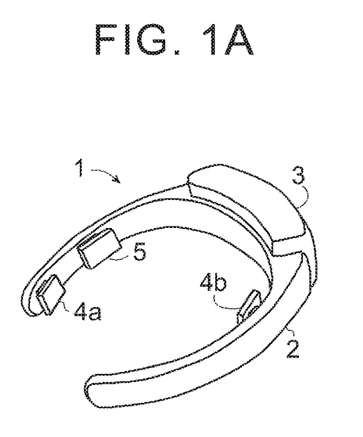
FIG. 1A is a schematic perspective view of a bio-information detecting apparatus of the present disclosure.
Figure 1B:
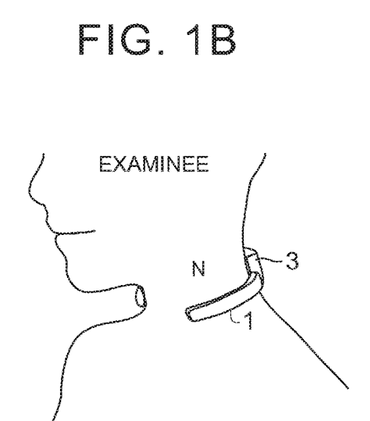
FIG. 1B is a schematic perspective view of the bio-information detecting apparatus of the present disclosure in a state of being attached around a neck part of an examinee.
Figures 1C, 1D:
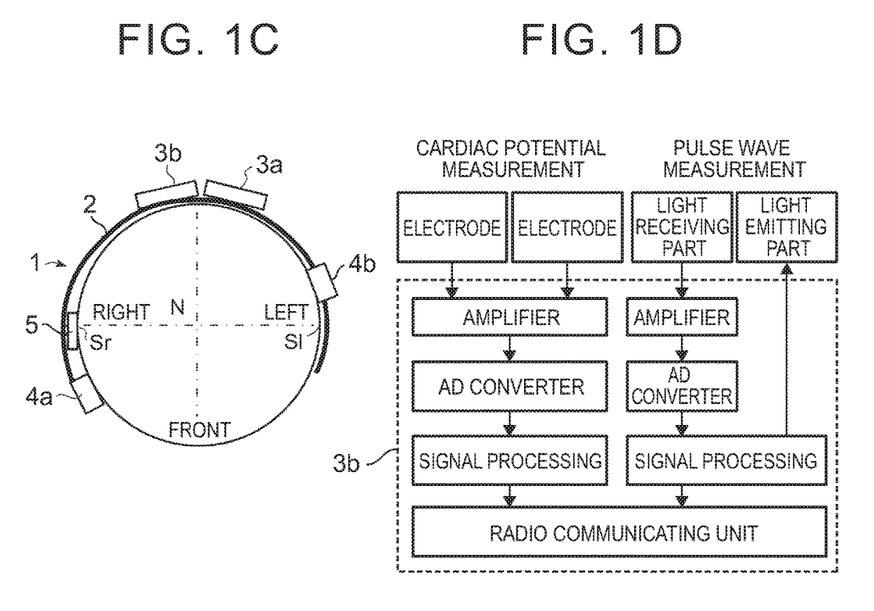
FIG. 1C is a schematic plan view of the bio-information detecting apparatus of the present disclosure.
FIG. 1D is a drawing illustrating an internal configuration of a signal flow of the bio-information detecting apparatus of the present disclosure in a block diagram.

With reference to FIG. 1A, a bio-information detecting apparatus 1 of the present disclosure includes, as a basic configuration thereof, a band member 2 curved in a substantially C-shape, and a pair of electrodes 4a, 4b for cardiac potential measurement fixed on an inner side of the C-shape of the band member 2, and an optical blood saturation measurement unit 5 for pulse wave measurement (referred to as a "pulse measurement unit," hereinafter). A signal processing unit 3 receives potential differences between the electrode 4a and the electrode 4b, and measurement values (light intensity received by a light receiving part as described later) of the pulse measurement unit 5, and includes a radio transmitting unit that transmits the above data to any external processing unit, and this signal processing unit 3 is fixed to the vicinity of the center portion of the C-shaped band member 2. The band member 2 may typically be formed by a flexible or elastic material, such as a plastic material or a resin material, or such as a plastic material or a resin material containing a metallic band-like member thereinside. The pair of electrodes 4a, 4b may be any electrode elements for cardiac potential measurement used in this field, and the pulse measurement unit 5 may be any (reflating-type) optical pulse measurement device (substrate including a light emitting part and the light receiving part) used in this field. The bio-information detecting apparatus 1 is a so-called neck-band type apparatus, and is configured, as schematically illustrated in FIG. 1B and FIG. 1C, such that the band member 2 to which the signal processing unit 3 is fixed is attached in such a manner that a center region of the C-shape of the band member 2 is disposed to a back side of a neck part N of an examinee, and the band member 2 extends along and surrounds the neck part N so that both ends of the C-shape reach respective positions more frontward than both lateral sides S1, Sr of the neck part N of the examinee. On the band member 2, the pair of electrodes 4a, 4b are arranged such that respective electrode surfaces come into contact with skin surfaces on the left and right of the neck part N in a state in which the bio-information detecting apparatus 1 is attached around the neck part N. The pulse measurement unit 5 is arranged with a measurement surface (the light emitting part and the light receiving part) thereof in contact with the skin surface of the neck part N in the state in which the bio-information detecting apparatus 1 is attached around the neck part N. The signal processing unit 3 includes, more specifically, a signal processing substrate 3b that receives and processes signals from the pair of electrodes 4a, 4b and the pulse measurement unit 5, and a battery 3a used for driving the electrodes 4a, 4b, the pulse measurement unit 5, and the signal processing substrate 3b.

Figure 2A:
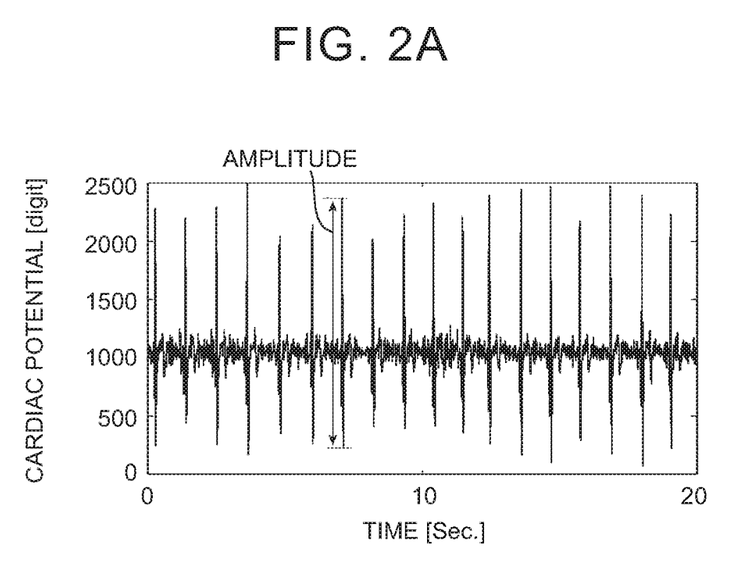
FIG. 2A shows an example of measurement data of cardiac potential measured by a pair of electrodes for cardiac potential measurement in the bio-information detecting apparatus of the present disclosure.
Figure 2B:
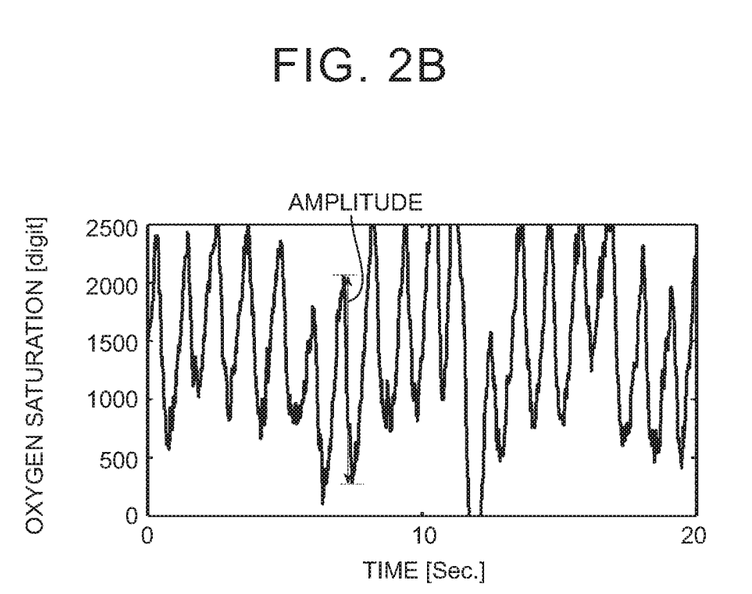
FIG. 2B shows an example of measurement data of an optical blood saturation measurement unit for pulse wave measurement in the bio-information detecting apparatus of the present disclosure.

The configuration of signal processing in the cardiac potential measurement and the optical pulse measurement in the bio-information detecting apparatus 1 of the aforementioned neck-band type may be any signal processing for cardiac potential measurement and pulse wave measurement. Briefly stated, as shown in FIG. 1D, the cardiac potential measurement is processed in such a manner that the potential difference between the pair of electrodes 4a and 4b in contact with the skin surfaces of the neck part N of the examinee is successively sent to an amplifier to be amplified, and digitized by an AD converter, and then is processed in the signal processing unit to be sent to any external processing unit. The potential difference obtained herein is cardiac potential oscillating in accordance with heartbeats, as shown in FIG. 2A. Meanwhile, in the optical pulse measurement, a light having a wavelength bandwidth to be absorbed into hemoglobin combined with oxygen in an arterial blood from the light emitting part provided on the measurement surface of the pulse measurement unit 5 in contact with the skin surface of the neck part N of the examinee is radiated onto a surface layer of the skin. In the above radiated light, a light reflected onto the surface layer of the skin without being absorbed into the hemoglobin combined with oxygen in the arterial blood is received by the light receiving part (also referred to as a reflecting-type pulse oxymeter). Signals indicating the light intensity of the light received by the light receiving part are successively sent to the amplifier to be amplified, digitalized by the AD converter, and is then processed in the signal processing unit to be sent to any external processing apparatus. As is well known in this field, the light intensity received by the light receiving part is proportional to amount of hemoglobin combined with oxygen in blood (oxygen saturation), and the amount of bloodstream hemoglobin becomes increased or decreased in accordance with the pulse. Hence, the light intensity received by the light receiving part oscillates, and these oscillations are correspondent to the pulse, as exemplified in FIG. 2B. Accordingly, the signals indicating the cardiac potential and the signals indicating the pulse are respectively transmitted from the radio communicating unit to any external processing apparatus.

As described in the section of the "Summary of the Disclosure," in the cardiac potential measurement and the optical pulse measurement of the bio-information detecting apparatus 1 attached around the neck part of the examinee in the aforementioned manner, one of the challenges to be achieved is how to improve the measurement sensitivity of the cardiac potential and the pulse oxygen saturation). In the successive cardiac potential data and pulse wave data as exemplified in FIG. 2A and FIG. 2B, as illustrated in these drawings, amplitudes of the oscillating waveforms are measured, occurrence of the oscillations, that is, occurrence of the heartbeats or the pulse is successively detected, and then the heart rate and the pulse rate are measured. With respect to this, in the cardiac potential measurement, the cardiac potential that has conventionally been measured at a chest part near the heart is measured at the neck part slightly apart from the heart, and thus the amplitude of the cardiac potential is decreased more than that in the case of measurement at the chest part near the heart. In the pulse measurement, change in blood flow rate in the artery is measured, but if the blood is pooled in the vessel, the blood flow rate becomes decreased, and thus the amplitude of the pulse (oxygen saturation) becomes decreased. In particular, because the bio-information detecting apparatus 1 is supposed to be attached around the neck part of the examinee, it is necessary to stably maintain the contact state of the electrodes and the pulse measurement unit with the skin surface even if the body of the examinee moves to some extent.

To cope with this, the inventors of the present disclosure have conducted various studies, and as a result, they have found a novel configuration capable of increasing measurement sensitivity of the cardiac potential and the pulse, in particular, the respective amplitudes of the cardiac potential and the pulse. Hereinafter, the novel configuration in the bio-information detecting apparatus 1 according to the present disclosure will be described.

Pressing Force of Pulse Measurement Unit

Figure 3A:
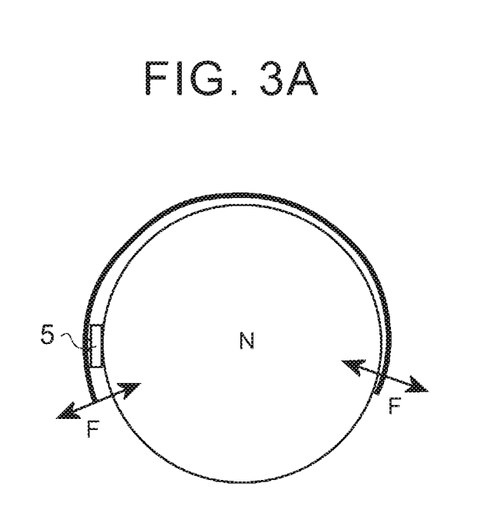
FIG. 3A shows a schematic side view showing a state in which the optical blood saturation measurement unit for pulse wave measurement in the bio-information detecting apparatus is pushed against a skin surface of a neck part of an examinee.
Figure 3B:
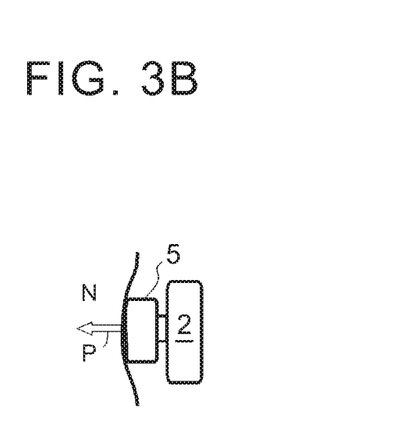
FIG. 3B is a schematic plan view showing the state in which the optical blood saturation measurement unit for pulse wave measurement in the bio-information detecting apparatus is pushed against the skin surface of the neck part of the examinee.

The aforementioned bio-information detecting apparatus 1 is positioned in a stable manner with an elastic force F (applied in a direction vertical to an extending direction of the neck part) of the band member 2 when the bio-information detecting apparatus 1 is attached around the neck part N of the examinee, as schematically illustrated FIG. 3A. In such a configuration, the pulse measurement unit 5 and the pair of electrodes 4a, 4b that are disposed on the C-shaped inner side of the band member 2 are pressed against the skin surface of the neck part N, as schematically illustrated in FIG. 3B. At this time, particularly in the pulse measurement, an excessively strong pressing force P causes reduction in blood flow rate due to pooled blood in the vessel, as aforementioned, and thus the measured sensitivity (magnitude of the amplitude of the pulse) becomes decreased. In addition, if the pressing force P is excessively weak, the band member 2 is likely to move, or the pulse measurement unit 5 is likely to be out of contact with the skin surface, and thus the measurement sensitivity also becomes decreased. To cope with this difficulty, there have been studies a preferable range of the pressing force to press the pulse measurement unit 5 against the skin surface in which a measurement value of the pulse measurement unit 5 falls within an acceptable range.

Figure 3C:
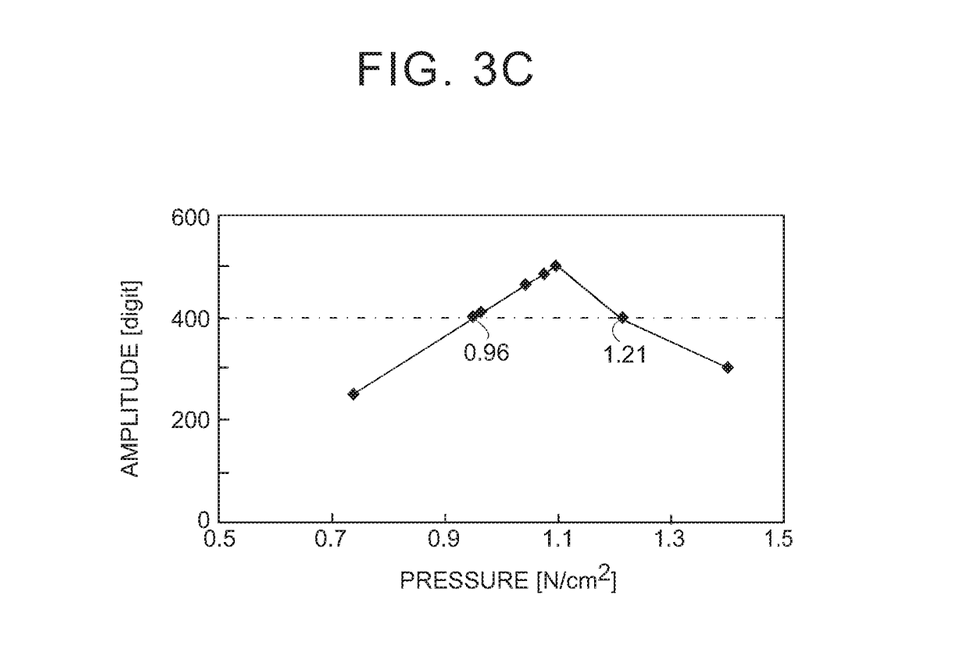
FIG. 3C shows respective pressure pressing forces of the optical blood saturation measurement unit for pulse wave measurement against the skin surface of the neck part and change in amplitude of measured pulse waves (blood saturation)

The bio-information detecting apparatus 1 using plural band members 2 with different elastic forces F was attached to the examinee an as to variously change the pressing force P of the pulse measurement unit 5 against the skin surface, and measure the pulse depending on the various pressing forces P by using the pulse measurement unit 5. As a result, change in amplitude (defined in FIG. 2B) obtained from the measurement data of the pulse depending on the various pressing forces exhibits a result as shown in FIG. 3C. In the drawing, each point "♦" represents a data plot, and a chain line represents a lower limit value of the acceptable amplitude.

As is understood with reference to this drawing, if the pressing force falls within a range of 0.96 to 1.21[N/cm$^2$], the amplitude becomes an acceptable value, and in particular, the amplitude becomes the maximum with the pressing force in the vicinity of 1.1[N/cm$^2$]. This pressing force is equivalent to a force to push down the skin surface by approximately 1 mm.

As described above, in the bio-information detecting apparatus 1 of the present invention, the dimension of the band member 2 is so defined as to apply the elastic force F of the band member 2 causing the pressing force of the pulse measurement unit 5 against the skin surface of the neck part that falls within a range of 0.96 to 1.21 [N/cm$^2$], more preferably, within orange of approximately 1.1[N/cm$^2$], thereby improving the sensitivity of the pulse measurement. A significant pressing force within the above range is applied from the pulse measurement unit 5 onto the neck part so that the apparatus having the band-like structure curved in a C-shape can be held relative to the neck part while preventing the apparatus from being out of position, which attains another advantage (it has been confirmed that the cardiac potential can be measured within the above pressing-force range if the following conditions of the configuration regarding the electrodes are satisfied).

Arrangement Configuration of Electrodes for Cardiac Potential Measurement

Based on the studies conducted by the inventors of the present disclosure, it has been found that the amplitude of measured cardiac potential is greatly affected by the arrangement of the pair of electrodes for cardiac potential measurement in a direction along the C-shape of the band member 2 (longitudinal direction of the band member 2), and in particular, if the electrode located on the right of the examinee is disposed relatively more frontward than the position of the electrode located on the left of the examinee, the cardiac potential amplitude becomes greatly increased compared with that in the other cases.

Figure 4A:
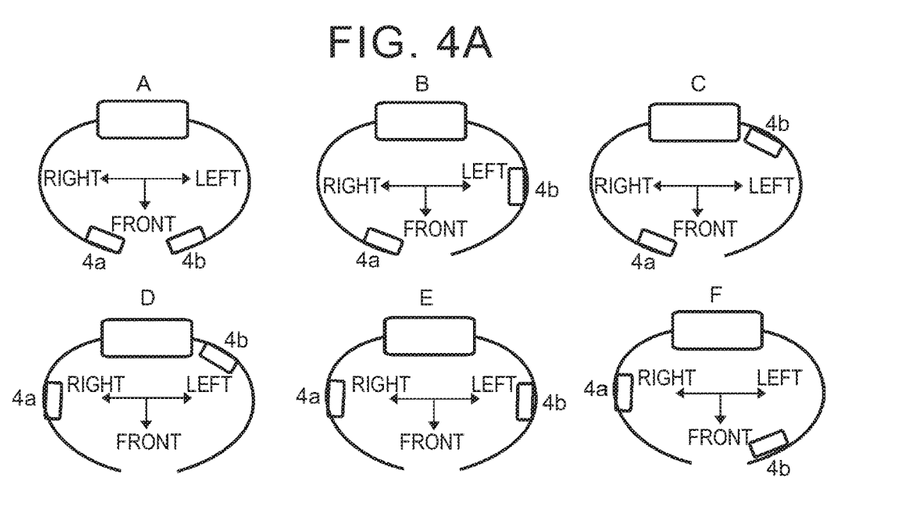
FIG. 4A is a drawing schematically showing various arrangement examples of the pair of electrodes for cardiac potential measurement in the bio-information detecting apparatus.
Figure 4B:
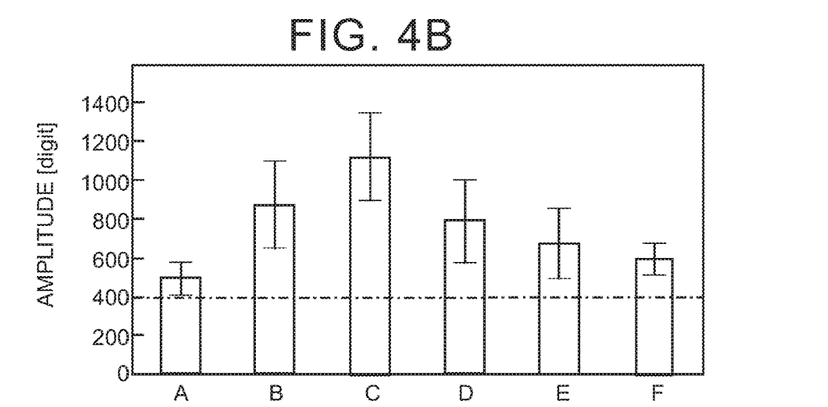
FIG. 4B shows respective amplitudes of the cardiac potential obtained by attaching the electrodes in the respective arrangement examples of FIG. 4A to the examinee.
Figure 4C:
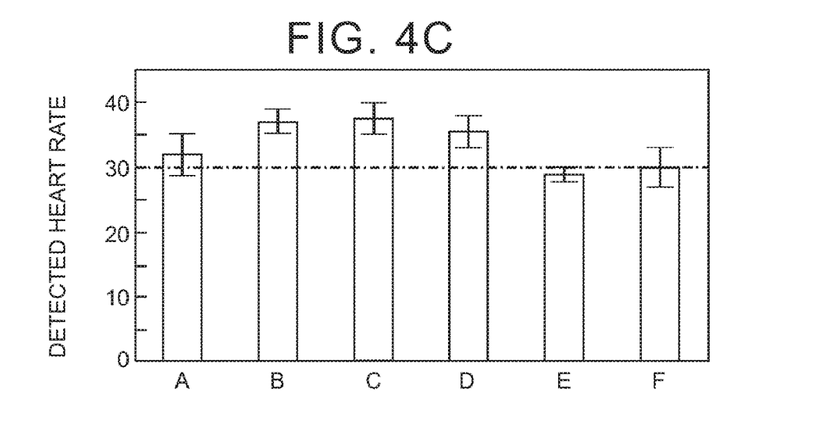
FIG. 4C shows respective heart rates detected by attaching the electrodes in the various arrangement examples of FIG. 4A to the examinee.

With reference to FIG. 4, each cardiac potential was measured by using the right and left electrodes against the neck part N in various arrangements A to F in the longitudinal direction of the band member 2, as shown in FIG. 4A; and magnitudes of the amplitudes as defined in FIG. 2A in measurement data and corresponding heart rates detected in the measurement data were results as respectively shown in FIG. 4B and FIG. 4C. These results indicate respective average values (bar graphs) and respective standard deviations (error bars) obtained from the measurement data for 30 seconds from three examinees. An electrode having a flat contact surface of 5 mm×5 mm was used as each electrode. Each of chain lines in the drawings indicates a lower limit of an acceptable value for each detected value in each vertical axis.

As is understood with reference to the results in the FIG. 4B and FIG. 4C, with respect to both the amplitude and the heart rate, each average value and each standard deviation are more than the respective acceptable values in the arrangements B, C, and D in FIG. 4A, that is, in the arrangement where the electrode 4a located on the right of the examinee was located relatively more frontward than the position of the electrode 4b on the left of the examinee. In particular, in the arrangement in which the right electrode 4a was located in a more frontward region than the lateral side of the neck part of the examinee, and in the arrangement in which the left electrode 4b was located more backward than the lateral side of the neck part of the examinee, the respective measurement values of both the amplitude and the heart rate become the maximum. In the bio-information detecting apparatus 1 of the present disclosure, it is possible to improve the measurement sensitivity of the cardiac potential by arranging the electrode located on the right of the examinee to be relatively more frontward than the position of the electrode located on the left of the examinee, more preferably, by arranging the electrode on the right of the examinee to be relatively more frontward than the lateral side of the neck part of the examinee, and also arranging the electrode on the left of the examinee to be relatively more backward than the lateral side of the neck part of the examinee. In general, the cardiac potential measurement is carried out with a method called as a 12-lead electrocardiography that measures cardiac potential by arranging electrodes on hands and feet of a human body with a heart surrounded by these electrodes. However, according to the present disclosure, the measurement is carried out by arranging the electrodes at the positions on the neck part where the heart is not surrounded by these electrodes. Accordingly, the present disclosure reveals, for the first time, the configuration capable of carrying out the cardiac potential measurement with high measurement sensitivity by arranging the pair of electrodes at positions that do not surround the heart.

Contact Surface Shape of Electrodes for Cardiac Potential Measurement

As aforementioned, the bio-information detecting apparatus 1 that is the subject matter of the present disclosure is a portable apparatus attached to the neck part of the examinee; therefore, it is preferable to stably maintain each contact of the electrodes for the cardiac potential measurement with the skin surface of the examinee regardless of body motions and postures of the examinee an as to measure the cardiac potential in a preferable manner. With respect to this point, as a solution for stably maintaining the contact state of each electrode with the skin surface, it can be expected to stabilize the contact of each electrode with the skin surface by configuring the contact surface of each electrode to have a center portion protruding toward the skin surface more than a peripheral edge of the contact surface. The inventors of the present disclosure have studied on this point, and have found that if the protrusion of the contact surface of each electrode (in a direction toward the skin surface) is as great as 2 mm, the measurement sensitivity to the cardiac potential becomes greatly decreased. With respect to the dimension of the contact surface of each electrode, since the bio-information detecting apparatus 1 as the subject matter of the present disclosure is attached around the neck part of the examinee, it is preferable to define the contact surface of each electrode to be as small as possible because a larger contact surface of each electrode causes a greater inconvenience to movement of the neck of the examinee. To the contrary, if each electrode has an excessively small dimension, and the contact area between the electrode and the skin surface becomes excessively small, it becomes difficult to measure the potential difference between the electrodes with a preferable sensitivity. To cope with this difficulty, there have been conducted studies on an upper limit of the protrusion of the contact surface and a lower limit of the contact area in each electrode where acceptable measurement data of the cardiac potential can be obtained.

Figure 5A:
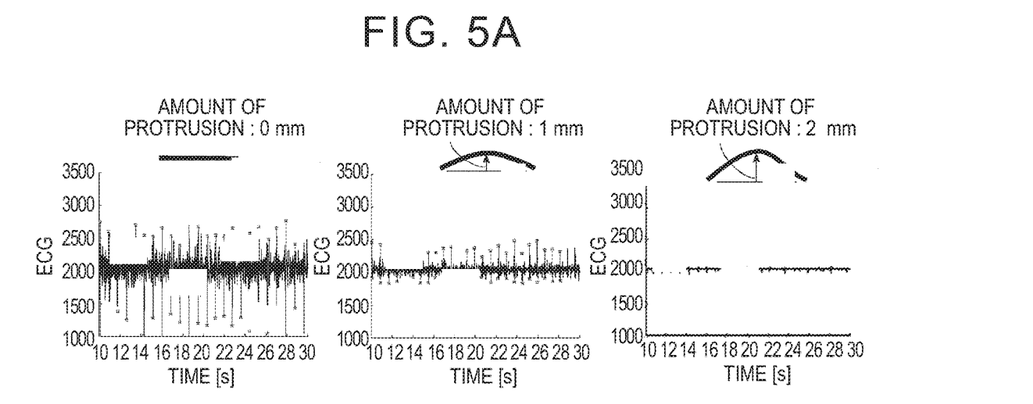
FIG. 5A is a drawing showing respective sectional shapes of contact surfaces in contact with the skin surface of the neck part of the examinee of each electrode for cardiac potential measurement in the bio-information detecting apparatus, and corresponding cardiac potential measurement examples.
Figure 5B:
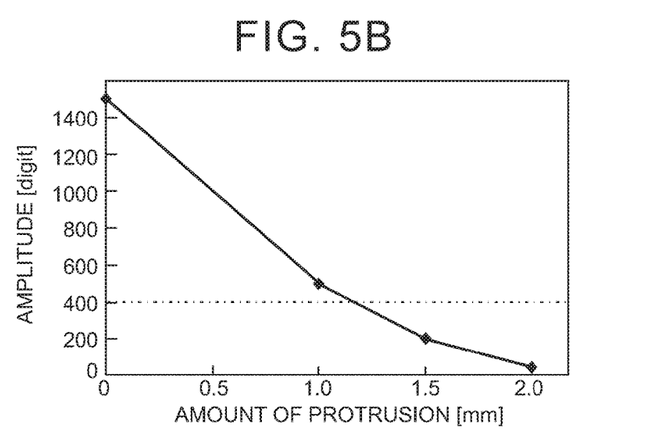
FIG. 5B shows change in amplitude of the cardiac potential measured depending on respective amounts of protrusion of a center portion relative to a peripheral edge of the contact surface of each electrode.
Figure 5C:
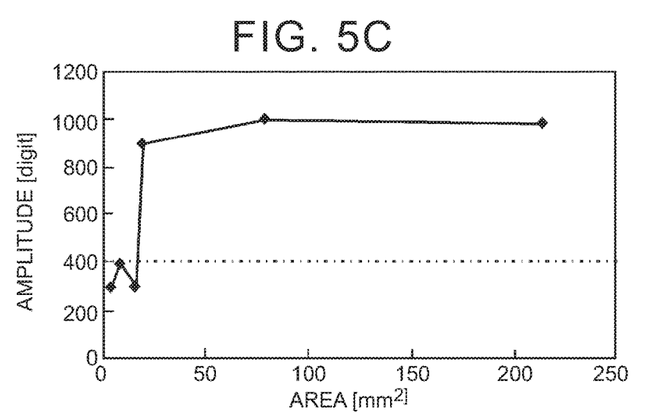
FIG. 5C shows change in amplitude of the cardiac potential measured depending on the respective areas of the contact surfaces of the electrode.

With respect to change in magnitude of the amplitude in the measurement data depending on the various protrusions of the contact surface of each electrode, as shown in FIG. 5B, it has been found that the amplitude becomes less than the acceptable level if the protrusion becomes more than 1 mm an electrode of 5 mm×5 mm was used as each electrode). With respect to change in magnitude of the amplitude in the measurement data depending on the various contact areas of the contact surface of each electrode, as shown in FIG. 5C, it has been found that the amplitude of the cardiac potential becomes significantly decreased if the contact area of each electrode with the skin surface of the neck part of the examinee becomes less than 25 $mm^2$ (an electrode having a flat contact surface was used as each electrode). Accordingly, in the bio-information detecting apparatus 1 of the present disclosure, there is employed an electrode formed to have a contact surface of which protrusion is not more than 1 mm, and of which contact area is not less than 25 $mm^2$ as each electrode so as to prevent the measurement sensitivity of the measurement data of the cardiac potential from becoming less than the acceptable level.

In the present embodiment, it should be appreciated that the bio-information detecting apparatus 1 may include only at least one of the pulse measurement unit and the pair of electrodes for the cardiac potential measurement. The bio-information detecting apparatus 1 of the present disclosure may be attached around a neck part of a vehicle driver so as to be used for measuring the heartbeats and the pulse of the driver during vehicle driving.

Although the above explanation has been made with respect to the embodiments of the present disclosure, it will be apparent for those skilled in the art that various modifications and changes are possible, and that the present disclosure is not limited to the above-illustrated embodiments, and may be applied to various devices and apparatuses without departing from the concepts of the present disclosure.

What is claimed is:

1. A bio-information detecting apparatus comprising:
   a band member curved in a C-shape, the band member configured to be attached in a manner as to extend along a neck part of an examinee from a back side of the neck part toward both left and right lateral sides of the neck part; and first and second electrodes configured for cardiac potential measurement of the examinee, the first electrode being disposed on the band member configured to come into contact with a right skin surface of the neck part of the examinee, and the second electrode being disposed on the band member configured to come into contact with a left skin surface of the neck part of the examinee, wherein the first electrode is provided at a first free end of the band member, and the second electrode is provided between a center of the band member and a second free end of the band member such that the first electrode is located relatively more frontward than the second electrode, and wherein the first electrode is configured to be disposed in a more frontward region than a center of the right lateral side of the neck part of the examinee based on its location on the band member, and the second electrode is configured to be disposed at a more backward position than a center of the left lateral side of the neck part of the examinee based on its location on the band member.

2. The bio-information detecting apparatus according to claim 1, further comprising:

a substrate having a light emitting part and a light receiving part each of which is configured to optically measure a blood oxygen saturation for pulse measurement of the examinee, the substrate disposed at a position on the band member configured to come into contact with the neck part of the examinee, wherein a pressing force of the substrate against the skin surface of the neck part is configured to be 0.96 to 1.21 [$N/cm^2$].

3. The bio-information detecting apparatus according to claim 1, wherein a contact surface of each of the first and second electrodes configured to come into contact with the skin surface of the neck part of the examinee is in a flat state or in a curved state in a direction in which a center portion of the contact surface protrudes more than a peripheral edge of the contact surface toward the skin surface of the neck part of the examinee not more than 1 mm.

4. The bio-information detecting apparatus according to claim 1, wherein a contact area of each of the first and second electrodes configured to come into contact with the skin surface of the neck part of the examinee is more than 25 $mm^2$.

5. The bio-information detecting apparatus according to claim 2, wherein the substrate is provided between the first end of the band member and the center of the band member.

6. A bio-information detecting apparatus comprising:

a band member curved in a C-shape, the band member configured to be attached in a manner as to extend along a neck part of an examinee from a back side of the neck part toward both left and right lateral sides of the neck part to a region more frontward than the left and right lateral sides of the neck part;

first and second electrodes configured for cardiac potential measurement of the examinee, the first electrode being disposed on the band member configured to come into contact with a right skin surface of the neck part of the examinee, and the second electrode being disposed on the band member configured to come into contact with a left skin surface of the neck part of the examinee; and a substrate disposed at a position on the band member configured to come into contact with the neck part of the examinee, the substrate having a light emitting part and a light receiving part that are configured to optically measure a blood oxygen saturation for pulse measurement of the examinee, wherein the first electrode is provided at a first free end of the band member, and the second electrode is provided between a center of the band member and a second free end of the band member such that the first electrode is located relatively more frontward than the second electrode, wherein the first electrode is configured to be disposed in a more frontward region than a center of the right lateral side of the neck part of the examinee based on its location on the band member, and the second electrode is configured to be disposed at a more backward position than a center of the left lateral side of the neck part of the examinee based on its location on the band member, and wherein a pressing force of the substrate against the skin surface of the neck part is configured to be 0.96 to 1.21 [$N/cm^2$].

7. The bio-information detecting apparatus according to claim 6, wherein the substrate is provided between the first end of the band member and the center of the band member.

* * * * *